United States Patent
Sharma

(10) Patent No.: US 11,817,193 B1
(45) Date of Patent: Nov. 14, 2023

(54) SYSTEMS AND METHODS FOR AUTOREGRESSIVE RECURRENT NEURAL NETWORKS FOR IDENTIFYING ACTIONABLE VITAL ALERTS

(71) Applicant: CADENCE SOLUTIONS, INC., New York, NY (US)

(72) Inventor: Ashwyn Sharma, Seattle, WA (US)

(73) Assignee: CADENCE SOLUTIONS, INC., New York, NY (US)

(*) Notice: Subject to any disclaimer, the term of this patent is extended or adjusted under 35 U.S.C. 154(b) by 0 days.

(21) Appl. No.: 18/171,078

(22) Filed: Feb. 17, 2023

(51) Int. Cl.
*G06N 3/04* (2023.01)
*G16H 10/60* (2018.01)
*G06N 3/0442* (2023.01)

(52) U.S. Cl.
CPC ........... *G16H 10/60* (2018.01); *G06N 3/0442* (2023.01)

(58) Field of Classification Search
CPC ..................................................... G16H 10/60
See application file for complete search history.

(56) References Cited

PUBLICATIONS

Weber et al. "Non-Autoregressive vs Autoregressive Neural Networks for System Identication", 2021, pp. 6, https://arxiv.org/abs/2105.02027.*
Ghazi et al. "CARRNN: A Continuous Autoregressive Recurrent Neural Network for Deep Representation Learning from Sporadic Temporal Data", 2021, pp. 11, https://arxiv.org/abs/2104.03739.*

* cited by examiner

*Primary Examiner* — Li Wu Chang
(74) *Attorney, Agent, or Firm* — DLA Piper LLP US

(57) ABSTRACT

An emerging service in the medical industry is to provide high quality remote care to patients by remotely monitoring patient vital information. In some instances, patient vitals information is collected at a much higher frequency in comparison to a traditional clinical environment. This frequent influx of patient health information can result in a considerable amount of health-related noise that health computing systems and clinicians must evaluate. The instant systems and methods leverage autoregressive recurrent neural networks and patient embeddings to predict the likelihood of needing to address certain patient information, thereby reducing the amount of health-related noise and to enable health computing systems and clinicians to use their resources more effectively.

17 Claims, 4 Drawing Sheets

SYSTEMS AND METHODS FOR AUTOREGRESSIVE RECURRENT NEURAL NETWORKS FOR IDENTIFYING ACTIONABLE VITAL ALERTS

BACKGROUND

In recent years, deep learning has become a fundamental part of the new generation of machine learning models due to the growing availability of data and computing power. Classical machine learning models, such as exponential smoothing models, implement feature engineering via manual processes comprised of supervised training on domain specific knowledge. However, supervised machine learning techniques are resource intensive, such that implementing a supervised approach may not be feasible in all circumstances.

For example, in the medical industry, the need for electronic medical records (EMR) has resulted in an exponential increase in the availability of electronic patient information. However, for stakeholders in the medical industry to effectively leverage such data in a supervised machine learning environment, this would require that said data be labeled and/or annotated and manually trained. Further, unlike data in other fields, EMR data can be esoteric (and therefore hard to label), unique to a small population of patients, irregular, and inherently noisy. As such, these properties can make supervised machine learning approaches an unreasonable solution for certain stakeholders that seek to extrapolate valuable insights from EMR data without investing in the manpower and computational resources required to implement such a solution. Accordingly, there is a need for systems and methods that overcome the deficiencies of prior art systems by enabling machine learning algorithms to interpret noisy data, and scale and learn in an unsupervised environment.

SUMMARY

In the healthcare industry, companies that provide healthcare services collect patient data, such as vitals (e.g., blood pressures, heart rates, weights, blood glucose, and the like) to deliver high quality remote care. In some instances, these vitals are collected at a much higher frequency as compared to the traditional clinical setting. In addition, healthcare companies may define thresholds for these vitals that fall outside of the typical parameters by which an alert is usually triggered for review by a clinician in a traditional clinical environment. For example, a systolic blood pressure that is over 180 triggers an alert to be reviewed by the clinician in a clinical environment. However, these static thresholds lead to a low signal to noise ratio (SNR) in the clinical environment as not requiring action by a clinician. As such, many of these alerts are dismissed by clinicians today without any action.

As discussed, attempting to extrapolate valuable insights from EMR data is particularly challenging, especially for machine learning techniques attempting to analyze noisy electronic patient data. Such challenges are further exacerbated in conventional supervised machine learning environments that can be difficult to scale and lack the agility to adapt to ever-changing esoteric patient data in real-time, which leads to ongoing signal to noise issues as data evolves. Therefore, as opposed to gleaning insights from EMR data from a machine learning algorithm in a supervised setting, the instant solution overcomes the deficiencies of conventional systems by leveraging an unsupervised machine learning model that leverages patient embeddings as an input to an autoregressive recurrent neural network that predicts the likelihood of an alert being dismissed by a clinician.

In particular, the system and methods described herein provide novel architecture and techniques for identifying actionable vital alerts using autoregressive recurrent neural networks. These techniques discussed herein overcome the deficiencies of such conventional approaches by at least configuring encoders for the specific type of data feature being ingested, cross-leveraging embeddings across separate machine learning tasks and domains, concatenating disparate embedding vectors into one singular vector, and training autoencoders on data/features with known characteristics. These novel solutions may additionally include an autoregressive recurrent neural network model that consumes input at various timesteps and produces a probability of a patient's vital(s) not leading to an actionable alert. This approach may be accomplished in part by passing the internal state of an autoregressive neural network to another autoregressive neural network at a previous or future time step and by identifying dependencies (e.g., patient vitals readings, local volatility, seasonality, and trends) and changes thereto between internal states. Indeed, by predicting the likelihood of an alert getting dismissed without requiring clinical action, such novel techniques improve the signal to noise ratio in a clinical environment by decreasing the computational resources necessary to monitor a patient and by reducing the number of reported alerts. Furthermore, these solutions drive clinical efficiency and enable clinicians to focus on prioritizing alerts that are more likely to require attention/review.

In one embodiment, a system comprising: a server comprising one or more processors and a non-transitory memory, in communication with the server, storing instructions that when executed by the one or more processors, cause the one or more processors to implement a method comprising: receiving one or more first patient embeddings as input for a first autoregressive recurrent neural network including a first internal state; generating, by the first autoregressive recurrent neural network, a first output, wherein the first output includes a probability of triggering a first actionable alert associated with patient vitals data; receiving one or more second patient embeddings, the first internal state, and first output, as input for a second autoregressive recurrent neural network including a second internal state; generating, by the second autoregressive recurrent neural network, a second output, wherein the second output includes a probability of triggering a second actionable alert associated with the patient vitals data; and identifying one or more dependencies associated with the first internal state and the second internal state.

In one embodiment, a computer-implemented method comprising: receiving one or more first patient embeddings as input for a first autoregressive recurrent neural network including a first internal state; generating, by the first autoregressive recurrent neural network, a first output, wherein the first output includes a probability of triggering a first actionable alert associated with patient vitals data; receiving one or more second patient embeddings, the first internal state, and first output, as input for a second autoregressive recurrent neural network including a second internal state; generating, by the second autoregressive recurrent neural network, a second output, wherein the second output includes a probability of triggering a second actionable alert associated with the patient vitals data; and identifying one or more dependencies associated with the first internal state and the second internal state.

In one embodiment, a non-transitory computer-readable medium storing instructions, that when executed by one or more processors, cause the one or more processors to implement the instructions for: receiving one or more first patient embeddings as input for a first autoregressive recurrent neural network including a first internal state; generating, by the first autoregressive recurrent neural network, a first output, wherein the first output includes a probability of triggering a first actionable alert associated with patient vitals data; receiving one or more second patient embeddings, the first internal state, and first output, as input for a second autoregressive recurrent neural network including a second internal state; generating, by the second autoregressive recurrent neural network, a second output, wherein the second output includes a probability of triggering a second actionable alert associated with the patient vitals data; and identifying one or more dependencies associated with the first internal state and the second internal state.

The disclosed principles are described with reference to analyzing patient vitals, but it should be understood that these principles may apply to any type of medical or clinical data wherein temporal features can be modeled using an autoregressive recurrent neural network. Accordingly, the disclosed principles are not limited to use with patient vitals and alerts.

DETAILED DESCRIPTION

Embodiments of the present disclosure relate to systems and methods for identifying actionable vital alerts using autoregressive recurrent neural networks. The implementation of these novel concepts may include, in one respect, leveraging an autoregressive recurrent neural network framework and patient embeddings to predict the likelihood of an alert being dismissed and/or reviewed by a clinician.

Figure 1:
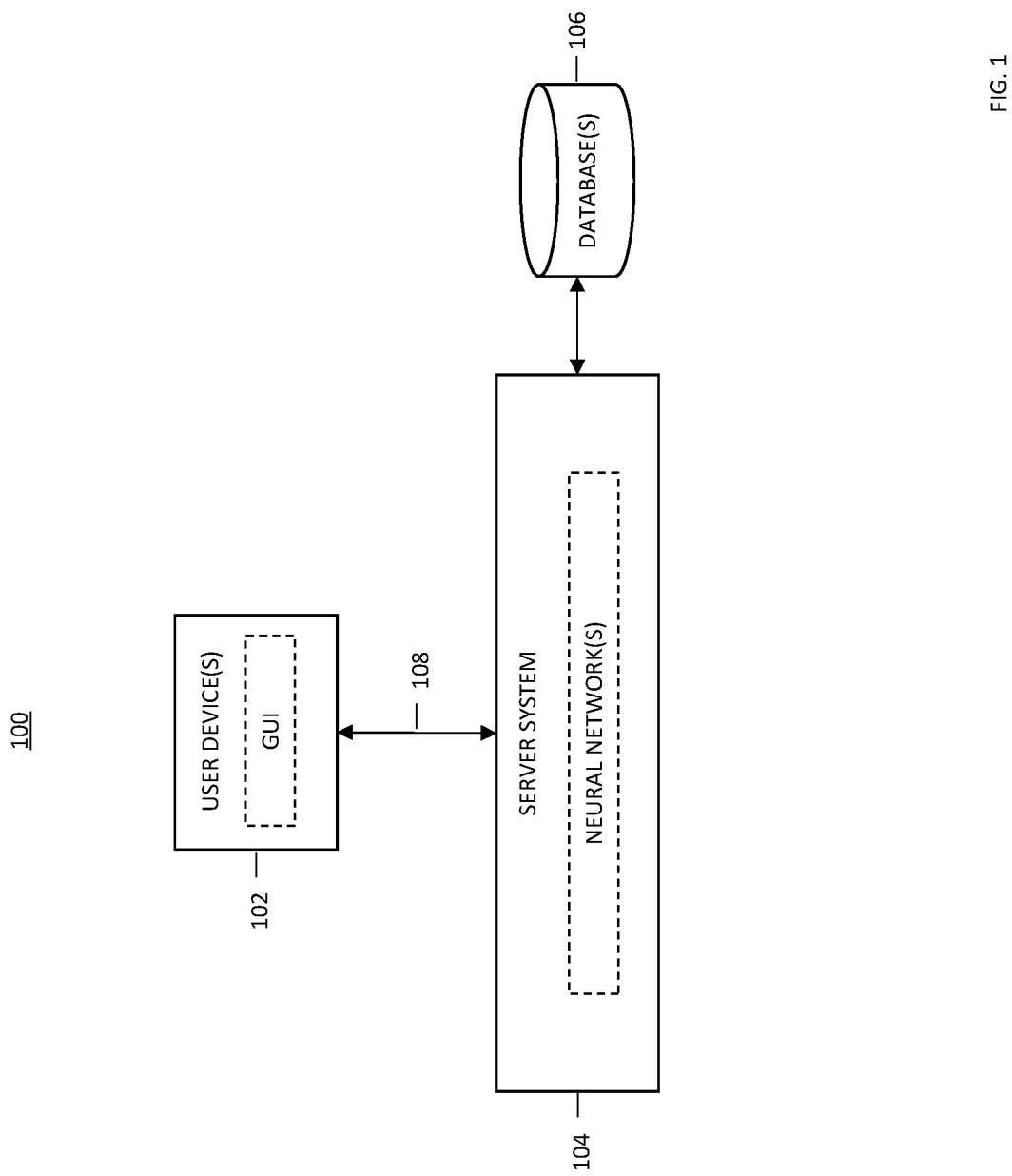
FIG. 1 illustrates a computing environment, according to various embodiments of the present disclosure.

Referring to FIG. 1, computing environment 100 may be configured to implement an autoregressive recurrent neural network for identifying vital alerts. Computing environment 100 may include one or more user device(s) 102, a server system 104, and one or more databases 106 communicatively coupled to the server system 104. The user device(s) 102, server system 104, and database(s) 106 may be configured to communicate through network 108.

In one or more embodiments, user device(s) 102 is operated by a user (e.g., a patient, a clinician, and/or an engineer). User device(s) 102 may be representative of mobile phones, smart phones, tablet computers, laptop computers, desktop computers, patient devices, server computers or any other computing device configured to capture, receive, store and/or disseminate any suitable data. Users may include, but are not limited to, individuals such as, for example, individuals, patients, clinicians, companies, prospective clients, and/or customers of an entity associated with server system 104, such as individuals who have received and/or monitor patient health information and are utilizing the services of, or consultation from, an entity associated with server system 104.

In some embodiments, a user device(s) 102 includes non-transitory memory, one or more processors including machine readable instructions, a communications interface which may be used to communicate with the server system (and, in some examples, with the database(s) 106), a user input interface for inputting data and/or information to the user device and/or a user display interface for presenting data and/or information on the user device. In some embodiments, the user input interface and the user display interface are configured as an interactive graphical user interface (GUI). The user device(s) 102 are also configured to provide the server system 104, via the interactive GUI, input information (e.g., patient information (e.g., vitals data, medicine information, biographical information, and demographic information) and documents such as patient records, patient charts, clinician notes, and diagnoses) for further processing. In some embodiments, the interactive GUI is hosted by the server system 104 or provided via a client application operating on the user device. In addition, the interactive GUI may include multiple distinct regions where results can be provided, feedback can be inputted, and clinical documents can be created, updated, and revised. In some embodiments, a user operating the user device(s) 102 may query server system 104 for information related to a received patient health information/documents (e.g., patient vitals information/a clinical document).

Server system 104 hosts, stores, and operates an autoregressive recurrent neural network and machine learning architecture for identifying actionable vital alerts and predicting the likelihood of an alert being dismissed or acted upon by a clinician. For example, server system 104 may include one or more recurrent neural networks and autoencoders for generating predictions related to patient vitals and capturing dependencies across the time dimension.

A first autoregressive neural network, including a first internal state, may automatically receive one or more first patient embeddings from a user device(s) 102 as input, wherein the one or more first patient embeddings are representative of one or more features including but not limited to: patient vitals, patient medicine information, patient symptom information, clinician notes regarding a patient, and patient biographical and demographic information. In response to receiving the patient embeddings, the first autoregressive recurrent neural network may generate a first output at the first internal state, wherein the first output includes a probability of triggering a first actionable alert associated with patient vitals data. A second autoregressive recurrent neural network including a second internal state may receive one or more second patient embeddings, the first internal state, and the first output, as input. For example, the first autoregressive recurrent neural network may transmit the first internal state and the first output to the second autoregressive recurrent neural network for further analysis. The second autoregressive recurrent neural network may generate a second output at the second internal state, wherein the second output includes a probability of triggering a second actionable alert associated with the patient vitals data. Server system 104 may then identify one or more dependencies associated with the first internal state and the second internal state. Notably, server system 104 is not limited to a first and second autoregressive recurrent neural networks and may include as many autoregressive recurrent neural networks as necessary to effectively model actionable vital alerts associated with patient vitals data.

The server system 104 may further generate instructions for displaying information related to an autoregressive recurrent neural network and/or one or more machine learning domain specific tasks via a GUI that operates on the user device(s) 102. The server system 104 may be further configured to implement two-factor authentication, Secure Sockets Layer (SSL) protocols for encrypted communication sessions, biometric authentication, and token-based authentication. The server system 104 may include one or more processors, servers, databases, communication/traffic routers, non-transitory memory, modules, and interface components.

Database(s) 106 may be locally managed and/or a cloud-based collection of organized data stored across one or more storage devices and may be complex and developed using one or more design schema and modeling techniques. In one or more embodiments, the database system may be hosted at one or more data centers operated by a cloud computing service provider. The database(s) 106 may be geographically proximal to or remote from the server system 104 configured for data dictionary management, data storage management, multi-user access control, data integrity, backup and recovery management, database access language application programming interface (API) management, and the like. The database(s) 106 are in communication with the server system 104 and the user device(s) 102 via network 108. The database(s) 106 stores various data, including training data for one or more autoencoders. In some instances, database(s) 106 can be modified via queries initiated by users operating user device(s) 102. In one or more embodiments, various data in the database(s) 106 will be refined over time to improve/teach one or more autoencoders, as discussed below with respect to FIGS. 2-4. In one or more embodiments, database(s) 106 additionally stores historical training data and clinical/medical/patient information used by various components in computing environment 100. Additionally, the database system may be deployed and maintained automatically by one or more components shown in FIG. 1.

Network 108 is any suitable network, including individual connections via the Internet, such as cellular or Wi-Fi networks. In some embodiments, network 108 connects terminals, services, and mobile devices using direct connections, such as radio frequency identification (RFID), near-field communication (NFC), Bluetooth™, low-energy Bluetooth™ (BLE), Wi-Fi™, ambient backscatter communication (ABC) protocols, Universal Serial Bus (USB), wide area network (WAN), local area network (LAN), or the Internet. Because the information transmitted may be personal or confidential, security concerns may dictate that one or more of these types of connection be encrypted or otherwise secured. In some embodiments, however, the information transmitted may be less personal and, therefore, the network connections may be selected for convenience over security.

For example, network 108 may be the Internet, a private data network, virtual private network using a public network and/or other suitable connection(s) that enables components in computing environment 100 to send and receive information between the components of computing environment 100.

Figure 2:
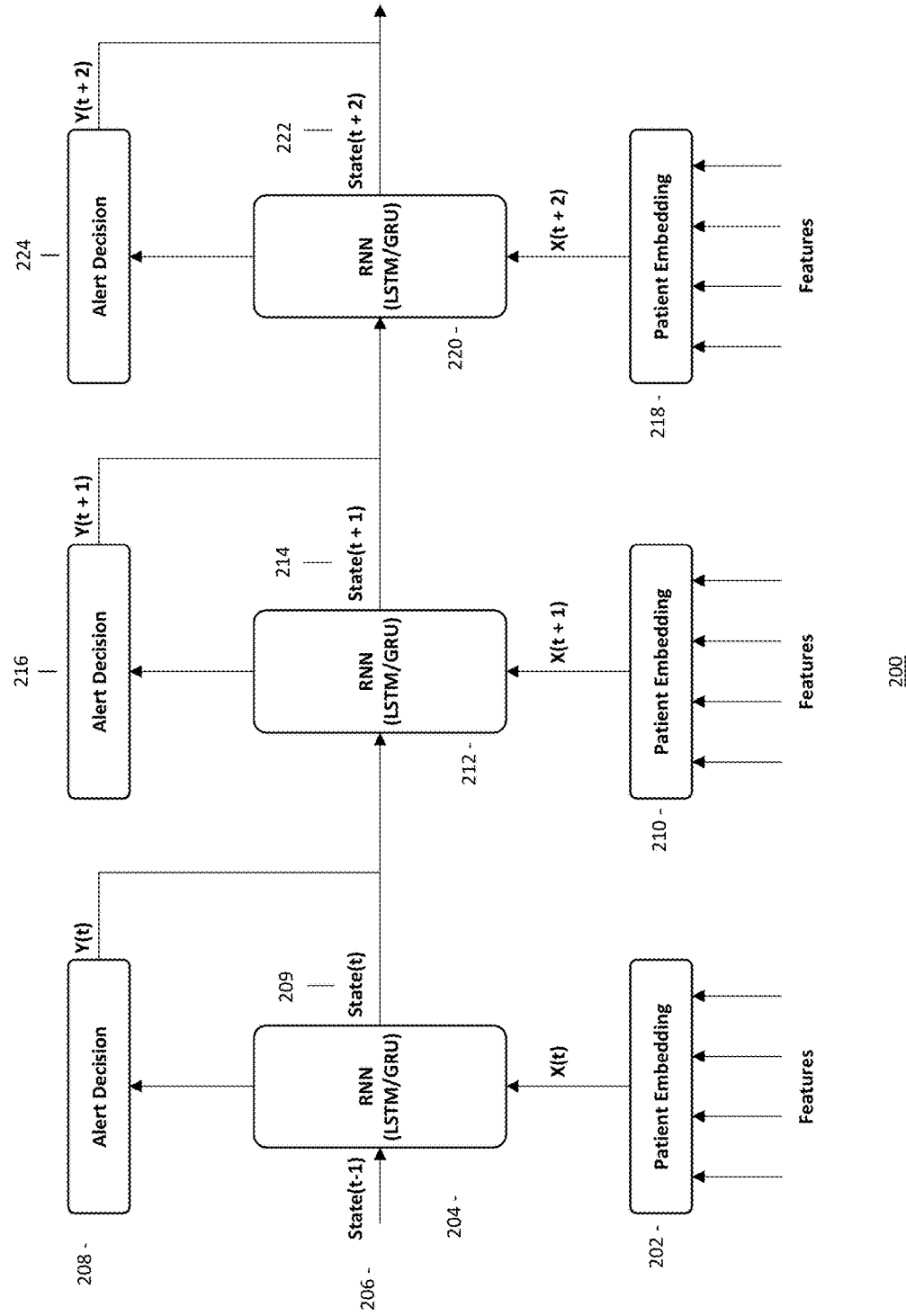
FIG. 2 illustrates an autoregressive recurrent neural network framework, according to various embodiments of the present disclosure.

FIG. 2 illustrates an autoregressive recurrent neural network framework 200, according to various embodiments of the present disclosure. The autoregressive recurrent neural network framework 200 may be associated with a clinical environment, wherein patient vitals information is received on a (predetermined/modifiable) periodic basis from patient(s) wearing medical devices (e.g., user device(s) 102) configured to capture information from the patient(s). The frequency in which the patient vitals information is received may be unique to the patient and/or unique to the type of vital information being monitored on the patient. In many clinical environments, as patients are being monitored, clinicians may set alerts associated with the patient's vitals, such that the alerts make the clinicians aware of abnormal activity when patient vitals information meets, exceeds, or drops below certain (static) thresholds. However, some alerts are dismissed by clinicians as not useful. These useless alerts add to the noise that clinical computing devices and clinicians must dedicate resources toward addressing.

The autoregressive recurrent neural network framework 200 is configured to generate output that would enable server system 104 to determine whether computational resources should be allocated to raising an alert, dismissing an alert, request patients or clinicians to take additional action (e.g., retake the patient's vital information), and the like. The autoregressive recurrent neural network framework 200 may be configured to implement any of the processes discussed herein in real-time, automatically, and/or in response to a command from a user operating a user device(s) 102 that are in communication with server system 104.

In a non-limiting capacity, autoregressive recurrent neural network framework 200 may include a first autoregressive recurrent neural network 204, a second autoregressive recurrent neural network 212, and a third autoregressive recurrent neural network 220. Although only three autoregressive recurrent neural networks are discussed, any number of autoregressive recurrent neural networks necessary to identify actionable patient vital alerts may be utilized. Each autoregressive recurrent neural network may include a long short term memory (LSTM) and/or a gated recurrent unit (GRU) and in some embodiments, further include an input gate, forget gate, and an output gate.

As depicted in FIG. 2, first autoregressive recurrent neural network 204 may receive first patient embeddings 202 (e.g., vector representations of patient vital information such as heart rate, blood pressure, and the like) as input (i.e., X(t)). In some instances, the first patient embedding 202 may be received from remote devices or from other components on server system 104. For example, first autoregressive recurrent neural network 204 may receive first patient embeddings 202 from an autoencoder configured for generating predictions, as depicted below in relation to FIG. 3.

The first autoregressive recurrent neural network 204 may additionally receive a past internal state 206 (i.e., State(t−1)) internal state as input. The internal state, for example past internal state 206 (i.e., State(t−1)), may include information indicating various variables that were used and/or not used in the process of generating an output. Each autoregressive recurrent neural network, via its respective input gate and forget, may determine the necessary information from the patient embeddings and internal states that are required to achieve a certain output. As discussed in more detail below, the ability of an autoregressive recurrent neural network to receive internal states from past, current, and future time steps (i.e., from autoregressive recurrent neural networks that precede or succeed in time relative to a current autoregressive recurrent neural network) improves the accuracy by which the autoregressive recurrent neural network can generate an output indicating whether a patient vital alert should be dismissed or acknowledged by a clinician.

The first autoregressive recurrent neural network 204 may be configured to generate a first output 208 (i.e., Y(t) as depicted in FIG. 2). In one instance, the first output 208 may be a probability of triggering a first actionable alert associated with the first patient embeddings 202. The first output 208 (i.e., a prediction) may be a probability (e.g., a value between one and zero) that is determined by converting vectors associated with the patient embeddings and one or more past internal state 206 (i.e., State(t−1)), first internal state 209 (State(t)), or future states (e.g., second internal state 214 or third internal state 222) (State(t+1) or State(t+2)), into a probability distribution. In one instance, the probability may represent a likelihood that a clinician would dismiss the patient vital alert in a clinical environment. An output, including first output 208 or any previous or subsequent output, may be calculated by using sigmoid function to assign a value between 0 and 1 followed by multiplying by a tanh function to decide its level of importance by assigning a value between −1 and 1.

The first internal state 209 and first output 208 may be passed to a second autoregressive recurrent neural network 212. As discussed in relation to first autoregressive recurrent neural network 204, second autoregressive recurrent neural network 212 may receive second patient embeddings 210 (i.e., X(t+1)), first internal state 209, and first output 208, as input and generate a second output 216 (i.e., Y(t+1)). Here, second autoregressive recurrent neural network 212, via its input gate, may discover/analyze and determine which information from the input should be kept; and, via its forget gate, determine which information should be discarded, such that the output gate can generate a probability related to raising patient vitals alert.

The second internal state 214 and second output 216 may be passed to a third autoregressive recurrent neural network 220. As discussed above, third autoregressive recurrent neural network 220 may receive third patient embeddings 218 (i.e., X(t+2)), second internal state 214, and second output 216, as input and generate a third output 224 (i.e., Y(t+2)).

Notably, one advantage of autoregressive recurrent neural network framework 200 is that server system 104 can identify dependencies between previous outputs (i.e., predictions related to patient vital alerts being dismissed or resolved in a modeled and/or clinical environment), current output, and/or future outputs. For example, a first autoregressive recurrent neural network may be configured to pass and receive present, current, and future internal states, such that information associated with patient vitals at a first internal state/first time step can be passed to a second autoregressive recurrent neural network having a second internal state/second time step. Further, as depicted in FIG. 2, the dependencies passed between autoregressive neural networks (e.g., the information transmitted from first internal state 209 State(t) to second internal state 214 State(t+1)) can be leveraged by server system 104 to interpret what caused a particular output (e.g., third output 224) to be generated by a specific autoregressive recurrent neural network (e.g., a third autoregressive recurrent neural network 220 that received the first internal state 209 State(t) and the second internal state 214 State(t+1) as depicted in FIG. 2), and further determine what information was beneficial in that determination. In response to this determination, an autoregressive recurrent neural network may be modified to better discover, use, or disregard certain input information, to improve the accuracy of generating an output.

Another advantage is that autoregressive recurrent neural network framework 200 enables alerts to be dismissed with better patient vital readings (i.e., modified patient vital monitoring parameters) and it is configured to automatically model real-time patient monitoring features like snoozing; for example, snoozing a resolved patient alert for a patient for certain amount of time: seconds, minutes, days, etc.

Figure 3:
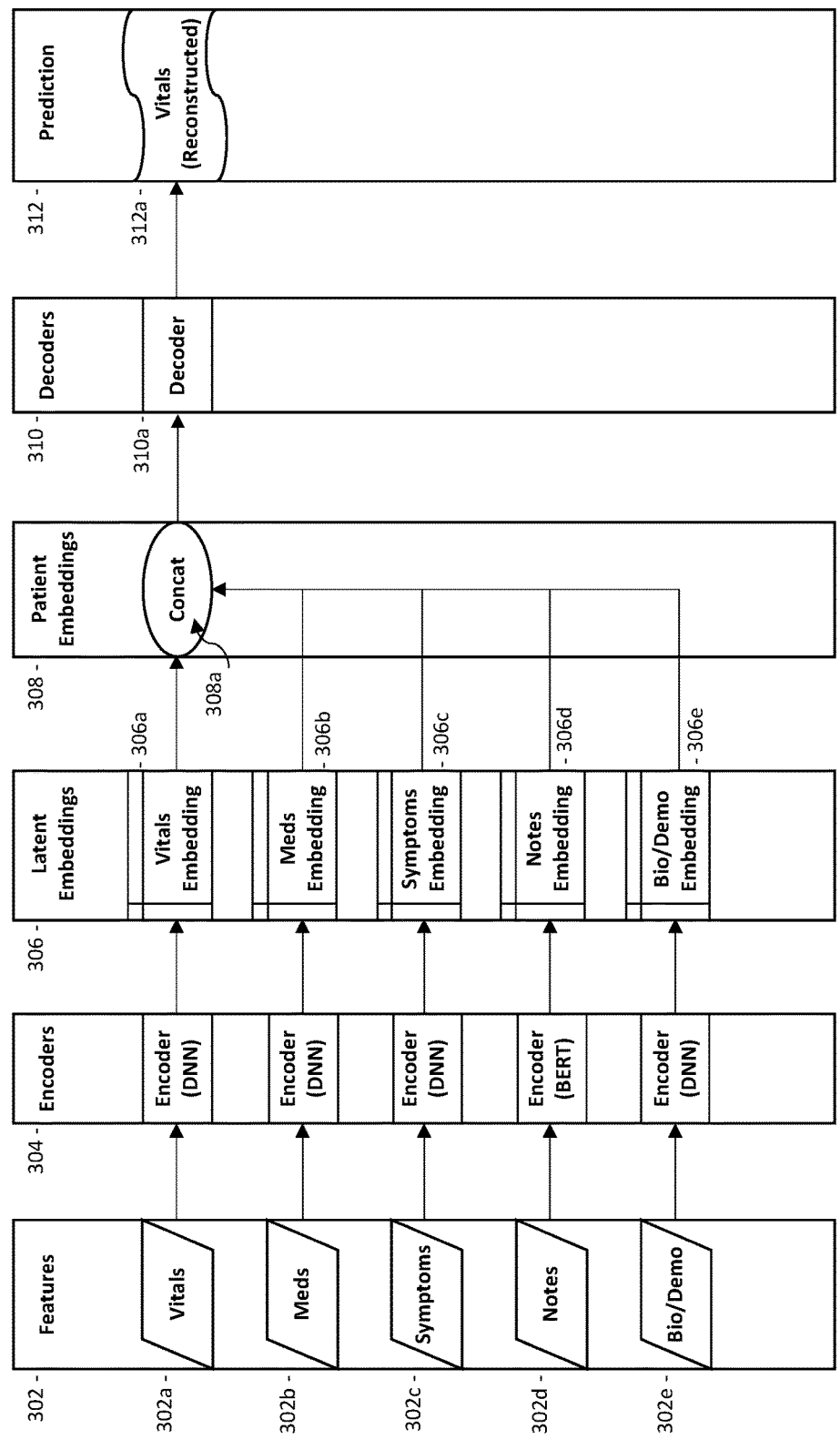
FIG. 3 illustrates autoencoder architecture for generating predictions, according to various embodiments of the present disclosure.

FIG. 3 illustrates autoencoder architecture for generating predictions 300, according to various embodiments of the present disclosure. As discussed in relation to the autoregressive recurrent neural network framework 200 in FIG. 2, the autoencoder architecture for generating predictions 300 may include encoders 304 and decoders 310. The autoencoder architecture for generating predictions 300 may be configured to implement a method for receiving one or more features 302 as input and reconstructing the one or more features 302 for real-time production or training purposes. In a non-limiting capacity, the one or more features 302 may include patient vitals information 302a, patient medicine information 302b (e.g., prescriptions), patient symptoms information 302c, notes 302d (e.g., patient or clinician notes regarding a patient), and/or patient biographical/demographic information 302e. Notably, the one or more features 302 may be of various different data types. Some of the features of the one or more features 302 may be numerical, for example, patient vitals information 302a may be numerical data that can be normalized. Other features may be categorical data, for example, patient medicine information 302b and patient symptoms information 302c may be categorical. Notes 302d may be text and in some instances patient symptoms information 302c may be of text data type (instead of, or in addition to, being a categorical data type). Patient biographical/demographic information 302e may consist of both numerical and categorical data types.

The one or more features 302 may be respectively transmitted to corresponding encoders 304. The encoders 304 may be specifically configured to handle the data type associated with the one or more features 302. For example, the encoder that receives patient vitals information 302a may be specifically configured to encode numerical data related to patient vitals (e.g., heart rate, blood pressure, and the like). In a non-limiting capacity, encoders 304 may be deep neural network encoders and in response to receiving the one or more features 302, the encoders 304 may convert the one or more features 302 into lower dimensional latent space representations 306 (i.e., latent embeddings). For example, regardless of each features' original data type, each of the one or more features 302 may be converted into its own respective embedding (i.e., vector). For example, patient vitals information 302a may be converted into patient vitals embeddings 306a. Similar conversions may be done to generate patient medicine embeddings 306b, patient symptoms embeddings 306c, notes embeddings 306d, and patient biographical/demographic information 306e. Notably, the lower dimensional latent space representations 306, in some instances, can be the vector representation of the semantic meaning of the one or more features 302.

The lower dimensional latent space representations 306 may then be concatenated 308a to form a singular patient embedding 308. Here, the lower dimensional latent space representations 306 may be aggregated and combined to form a singular patient embedding 308 (e.g., a vector). The singular patient embedding 308 can be indicative of a holistic representation of a patient's state (e.g., health) at a given point in time.

The decoders 310 may receive the singular patient embedding 308, wherein it is configured to reconstruct one or all of the one or more features 302 based on the singular patient embedding 308. For example, the now concatenated singular patient embedding 308 may be passed to decoder 310a to reconstruct one or more of the one or more features. In one instance, despite the singular patient embedding including vectors related to each of the one or more features 302, the decoders 310 may be configured to only reconstruct the patient vitals information 302a, such that a prediction 312 including reconstructed patient vitals 312a is generated.

The autoencoder architecture for generating predictions 300, in conjunction with one or more components interacting with computing environment 100, may generate a reconstruction error, which is the difference between initial input vectors (i.e., vector representation of the one or more features 302/patient vitals information 302a) and output generated by decoders 310 (i.e., predictions 312/reconstructed patient vitals 312a). In the event autoencoder architecture for generating predictions 300 is being trained, one objective would be to reduce the reconstruction error in order to improve the accuracy of decoder 310 reconstructed input.

Figure 4:
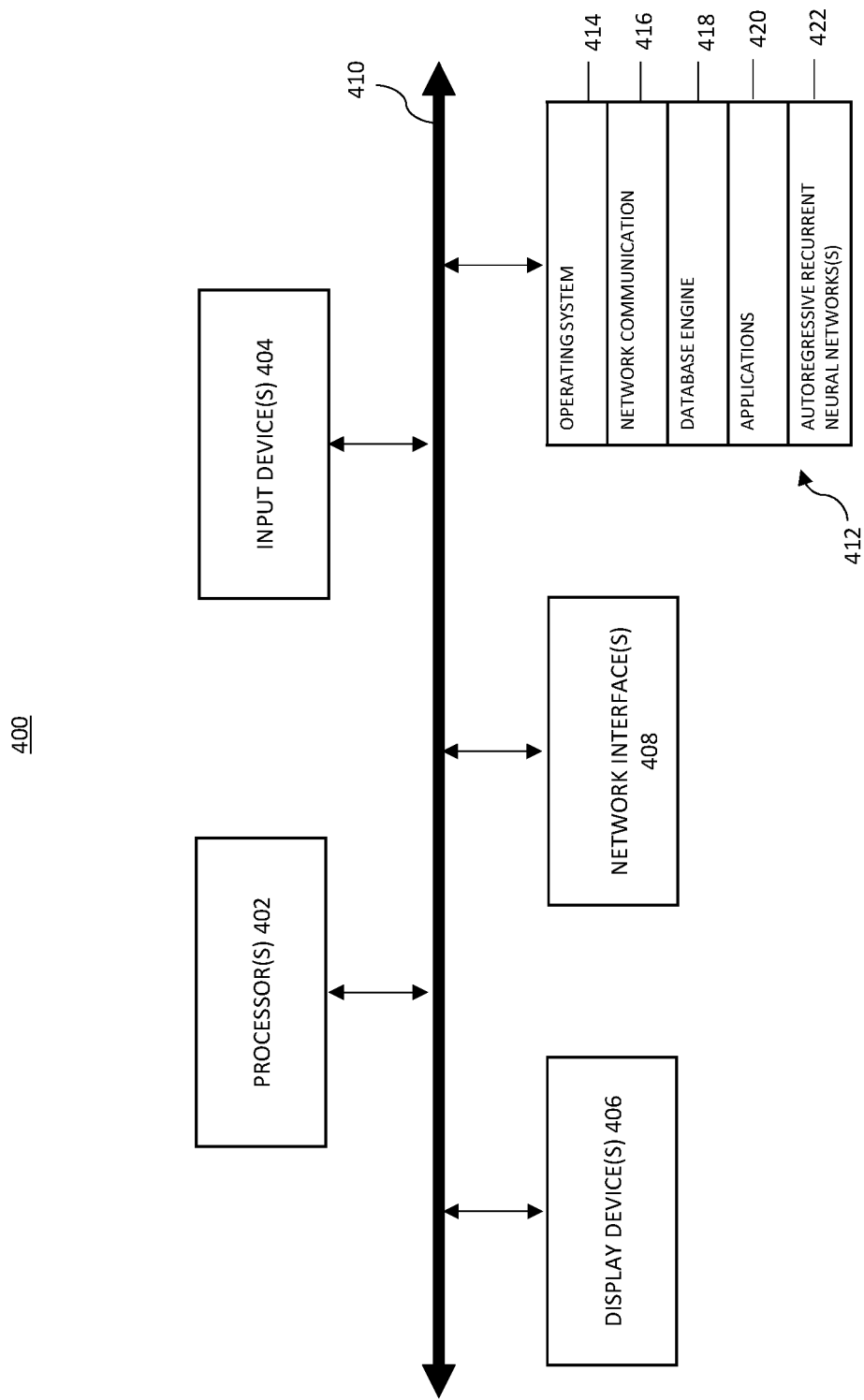
FIG. 4 illustrates a block diagram for a computing device, according to various embodiments of the present disclosure.

FIG. 4 illustrates a block diagram for a computing device, according to various embodiments of the present disclosure. For example, computing device 400 may function as server system 104. The computing device 400 may be implemented on any electronic device that runs software applications derived from compiled instructions, including without limitation personal computers, servers, smart phones, media players, electronic tablets, game consoles, and email devices. In some implementations, the computing device 400 may include processor(s) 402, input device(s) 404, display device(s) 406, network interfaces 408, and computer-readable medium(s) 412 storing software instructions. Each of these components may be coupled by bus 410, and in some embodiments, these components may be distributed among multiple physical locations and coupled by a network 108.

Display device(s) 406 may be any known display technology, including but not limited to display devices using Liquid Crystal Display (LCD) or Light Emitting Diode (LED) technology. Processor(s) 402 may use any known processor technology, including but not limited to graphics processors and multi-core processors. Input device(s) 404 may be any known input device technology, including but not limited to a keyboard (including a virtual keyboard), mouse, track ball, camera, and touch-sensitive pad or display. Bus 410 may be any known internal or external bus technology, including but not limited to industry standard architecture (ISA), extended industry standard architecture EISA, peripheral component interconnect (PCI), PCI Express, universal serial bus (USB), Serial advanced technology attachment (ATA), or FireWire. Computer-readable medium(s) 412 may be any non-transitory medium that participates in providing instructions to processor(s) 402 for execution, including without limitation, non-volatile storage media (e.g., optical disks, magnetic disks, flash drives, etc.), or volatile media (e.g., SDRAM, ROM, etc.).

Computer-readable medium(s) 412 may include various instructions for implementing an operating system 414 (e.g., Mac OS®, Windows®, Linux). The operating system may be multi-user, multiprocessing, multitasking, multithreading, real-time, and the like. The operating system may perform basic tasks, including but not limited to: recognizing input from input device(s) 404; sending output to display device(s) 406; keeping track of files and directories on computer-readable medium(s) 412; controlling peripheral devices (e.g., disk drives, printers) which can be controlled directly or through an input/output (I/O) controller; and managing traffic on bus 410. Network communications instructions 416 may establish and maintain network connections (e.g., software for implementing communication protocols, such as TCP/IP, HTTP, Ethernet, telephony).

Database processing engine 418 may include instructions that enable computing device 400 to implement one or more methods as described herein. Application(s) 420 may be an application that uses or implements the processes described herein and/or other processes. The processes may also be implemented in operating system 414. For example, application(s) 420 and/or operating system 414 may execute one or more operations configured one or more autoregressive recurrent neural networks 422 used in conjunction with one or more methods as described above.

The described features may be implemented in one or more computer programs that may be executable on a programmable system including at least one programmable processor coupled to receive data and instructions from, and to transmit data and instructions to a data storage system (e.g., database(s) 106), at least one input device, and at least one output device. A computer program is a set of instructions that can be used, directly or indirectly, in a computer to perform a certain activity or bring about a certain result. A computer program may be written in any form of programming language (e.g., Tensorflow, Keras, PyTorch, Cognitive Toolikit, Janusgraph, Gremlin, Sandbox, SQL, Objective-C, Java), including compiled or interpreted languages, and it may be deployed in any form, including as a stand-alone program or as a module, component, subroutine, or other unit suitable for use in a computing environment.

Suitable processors for the execution of a program of instructions may include, by way of example, both general and special purpose microprocessors, and the sole processor or one of multiple processors or cores, of any kind of computer. Generally, a processor may receive instructions and data from a read-only memory or a random-access memory or both. The essential elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data may include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

To provide for interaction with a user, the features may be implemented on a computer having a display device such as an LED or LCD monitor for displaying information to the user and a keyboard and a pointing device such as a mouse or a trackball by which the user can provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination thereof. The components of the system may be connected by any form or medium of digital data communication such as a communication network. Examples of communication networks include, e.g., a telephone network, a LAN, a WAN, and the computers and networks forming the Internet.

The computer system may include clients and servers. A client and server may generally be remote from each other and may typically interact through a network. The relationship of client and server may arise by virtue of computer programs running on the respective computers and having a client-server relationship to each other.

One or more features or steps of the disclosed embodiments may be implemented using an API. An API may define one or more parameters that are passed between a calling application and other software code (e.g., an operating system, library routine, function) that provides a service, that provides data, or that performs an operation or a computation.

The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer will employ to access functions supporting the API.

In some implementations, an API call may report to an application the capabilities of a device running the application, such as input capability, output capability, processing capability, power capability, communications capability, etc.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

It is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

What is claimed is:

1. A system comprising:
   a server comprising one or more processors; and
   a non-transitory memory, in communication with the server, storing instructions that when executed by the one or more processors, cause the one or more processors to implement a method comprising:
   receiving one or more first patient embeddings as input for a first autoregressive recurrent neural network including a first internal state;
   generating, by the first autoregressive recurrent neural network, a first output, wherein the first output includes a probability of triggering a first actionable alert associated with patient vitals data;
   receiving one or more second patient embeddings, the first internal state, and first output, as input for a second autoregressive recurrent neural network including a second internal state, wherein the second autoregressive recurrent neural network is configured to receive the second internal state and a third future internal state as input;
   generating, by the second autoregressive recurrent neural network, a second output, wherein the second output includes a probability of triggering a second actionable alert associated with the patient vitals data; and
   identifying one or more dependencies associated with the first internal state and the second internal state.

2. System of claim 1, wherein the one or more first patient embeddings are associated with one or more patient vitals information.

3. The system of claim 1, wherein the one or more first patient embeddings are received from an autoencoder configured for predicting patient vitals information.

4. The system of claim 1, wherein the first output is generated by converting vectors associated with the one or more first patient embeddings into a probability distribution.

5. The system of claim 1, wherein identifying one or more dependencies, further comprises analyzing the first output, the second output, and a third future output, for information that was utilized and disregarded in order to generate the first output and the second output.

6. The system of claim 1, wherein the first autoregressive recurrent neural network and the second autoregressive recurrent neural network include a long short term memory unit.

7. A computer-implemented method comprising:
   receiving one or more first patient embeddings as input for an autoregressive recurrent neural network at a current state;
   receiving one or more first patient embeddings as input for a first autoregressive recurrent neural network including a first internal state;
   generating, by the first autoregressive recurrent neural network, a first output, wherein the first output includes a probability of triggering a first actionable alert associated with patient vitals data;
   receiving one or more second patient embeddings, the first internal state, and first output, as input for a second autoregressive recurrent neural network including a second internal state, wherein the second autoregressive recurrent neural network further receives the second internal state and a third future internal state as input;

generating, by the second autoregressive recurrent neural network, a second output, wherein the second output includes a probability of triggering a second actionable alert associated with the patient vitals data; and identifying one or more dependencies associated with the first internal state and the second internal state.

8. The computer-implemented method of claim 7, wherein the one or more first patient embeddings are associated with one or more patient vitals information.

9. The computer-implemented method of claim 7, wherein the one or more first patient embeddings are received from an autoencoder configured for predicting patient vitals information.

10. The computer-implemented method of claim 7, wherein the first output is generating by converting vectors associated with the one or more first patient embeddings into a probability distribution.

11. The computer-implemented method of claim 7, wherein identifying one or more dependencies, further comprises analyzing the first output, the second output, and a third future output, for information that was utilized and disregarded in order to generate the first output and the second output.

12. The computer-implemented method of claim 7, wherein the first autoregressive recurrent neural network and the second autoregressive recurrent neural network include a long short term memory unit.

13. A non-transitory computer-readable medium storing instructions, that when executed by one or more processors, cause the one or more processors to implement the instructions for:

receiving one or more first patient embeddings as input for a first autoregressive recurrent neural network including a first internal state;

generating, by the first autoregressive recurrent neural network, a first output, wherein the first output includes a probability of triggering a first actionable alert associated with patient vitals data;

receiving one or more second patient embeddings, the first internal state, and first output, as input for a second autoregressive recurrent neural network including a second internal state, wherein the second autoregressive recurrent neural network further receives the second internal state and a third future internal state as input;

generating, by the second autoregressive recurrent neural network, a second output, wherein the second output includes a probability of triggering a second actionable alert associated with the patient vitals data; and identifying one or more dependencies associated with the first internal state and the second internal state.

14. The non-transitory computer-readable medium of claim 13, wherein the one or more first patient embeddings are associated with one or more patient vitals information.

15. The non-transitory computer-readable medium of claim 13, wherein the one or more first patient embeddings are received from an autoencoder configured for predicting patient vitals information.

16. The non-transitory computer-readable medium of claim 13, wherein the first output is generated by converting vectors associated with the one or more first patient embeddings into a probability distribution.

17. The non-transitory computer-readable medium of claim 13, wherein identifying one or more dependencies, further comprises analyzing the first output, the second output, and a third future output, for information that was utilized and disregarded in order to generate the first output and the second output.

* * * * *